(12) United States Patent
Skipper

(10) Patent No.: US 8,216,258 B2
(45) Date of Patent: Jul. 10, 2012

(54) MEDICAL CLAMP AND METHOD OF USE

(76) Inventor: Ted Robert Skipper, Boring, OR (US)

( * ) Notice: Subject to any disclaimer, the term of this patent is extended or adjusted under 35 U.S.C. 154(b) by 465 days.

(21) Appl. No.: 12/380,418

(22) Filed: Feb. 27, 2009

(65) Prior Publication Data
US 2010/0222793 A1 Sep. 2, 2010

(51) Int. Cl.
*A61B 17/122* (2006.01)
*A61B 17/08* (2006.01)
(52) U.S. Cl. .............. 606/151; 600/41; 24/502; 24/509; 24/514
(58) Field of Classification Search .............. 24/502, 24/509, 514; 132/251, 252, 277; 285/364–368, 285/373, 406–413, 419–420; 600/573, 39, 600/41, 29, 37; 604/174; 128/842–844; 606/151, 157, 158, 205–211, 153, 156, 144, 606/148, 232; 403/289–290
See application file for complete search history.

(56) References Cited

U.S. PATENT DOCUMENTS

| 2,225,875 | A | * | 12/1940 | Liebmann | ............ | 24/72.5 |
| 4,032,100 | A | * | 6/1977 | Kahn | ............ | 248/211 |
| 4,624,272 | A | * | 11/1986 | Franzino | ............ | 132/251 |
| 2004/0182411 | A1 | * | 9/2004 | Rogers et al. | ............ | 132/277 |

FOREIGN PATENT DOCUMENTS
EP      283305 A1 * 9/1988
* cited by examiner

*Primary Examiner* — Kathleen Sonnett
*Assistant Examiner* — Rachel S Papeika
(74) *Attorney, Agent, or Firm* — Mark S. Hubert

(57) ABSTRACT

A design of a medical clamp is provided that offers improved retention to and gripping of a patient's appendages through an open ended tubular design. The inside of the clamp has a taper approximating human dimensions. The interior has a reticulated surface for enhanced gripability. The exterior is ribbed for patient gripability and air circulation. A condom catheter retention ring is provided along the outer top periphery. The clamp is of a split design with matingly engageable hinge halves held together with a roll pin and forced into its tubular configuration by a spring that pushes against wing extensions projecting from each clamp half. A thumb screw spans the space between the two halves and allows adjustment of the spring pressure as well as defining the closed diameter of the clamp.

6 Claims, 6 Drawing Sheets

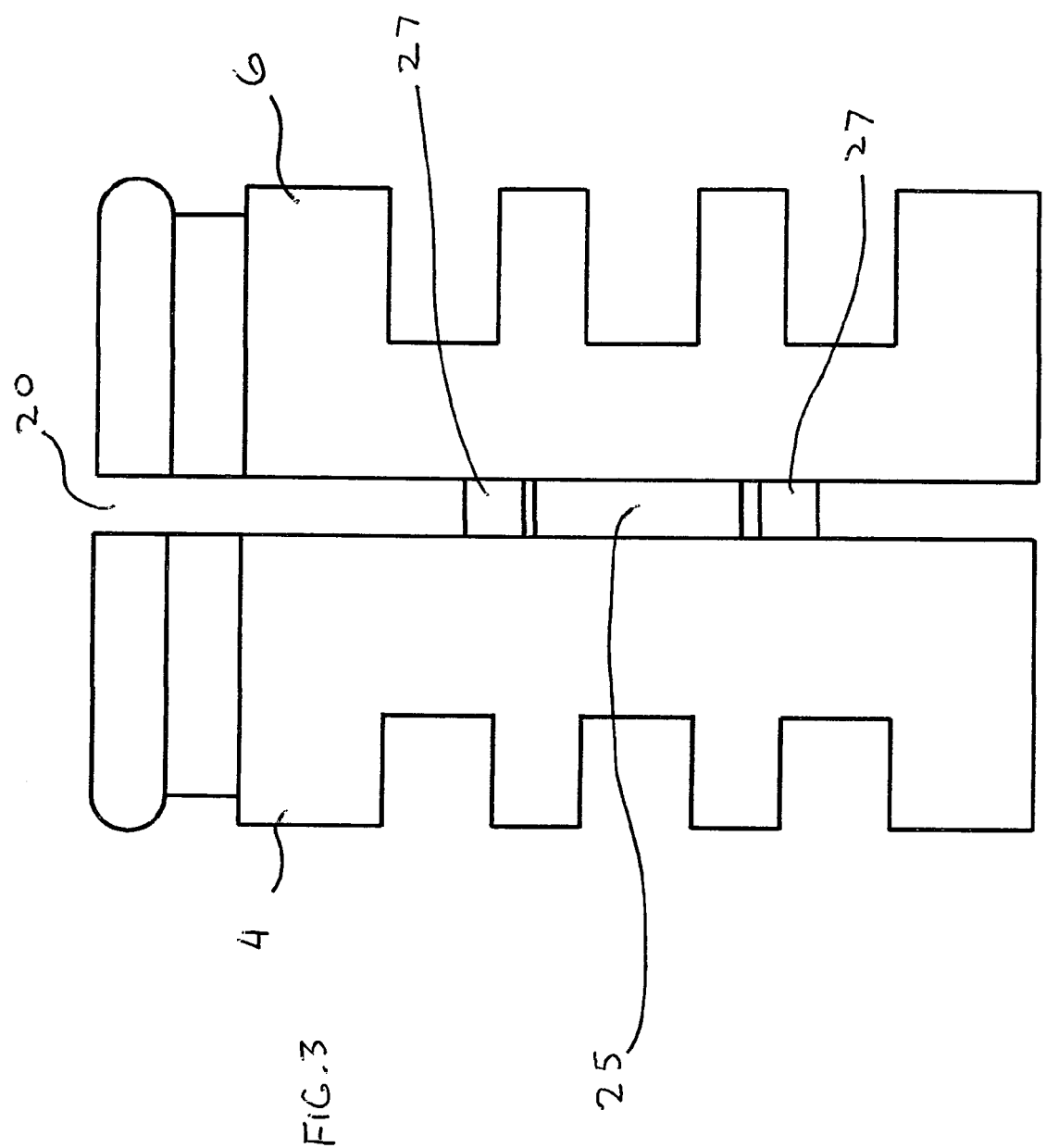

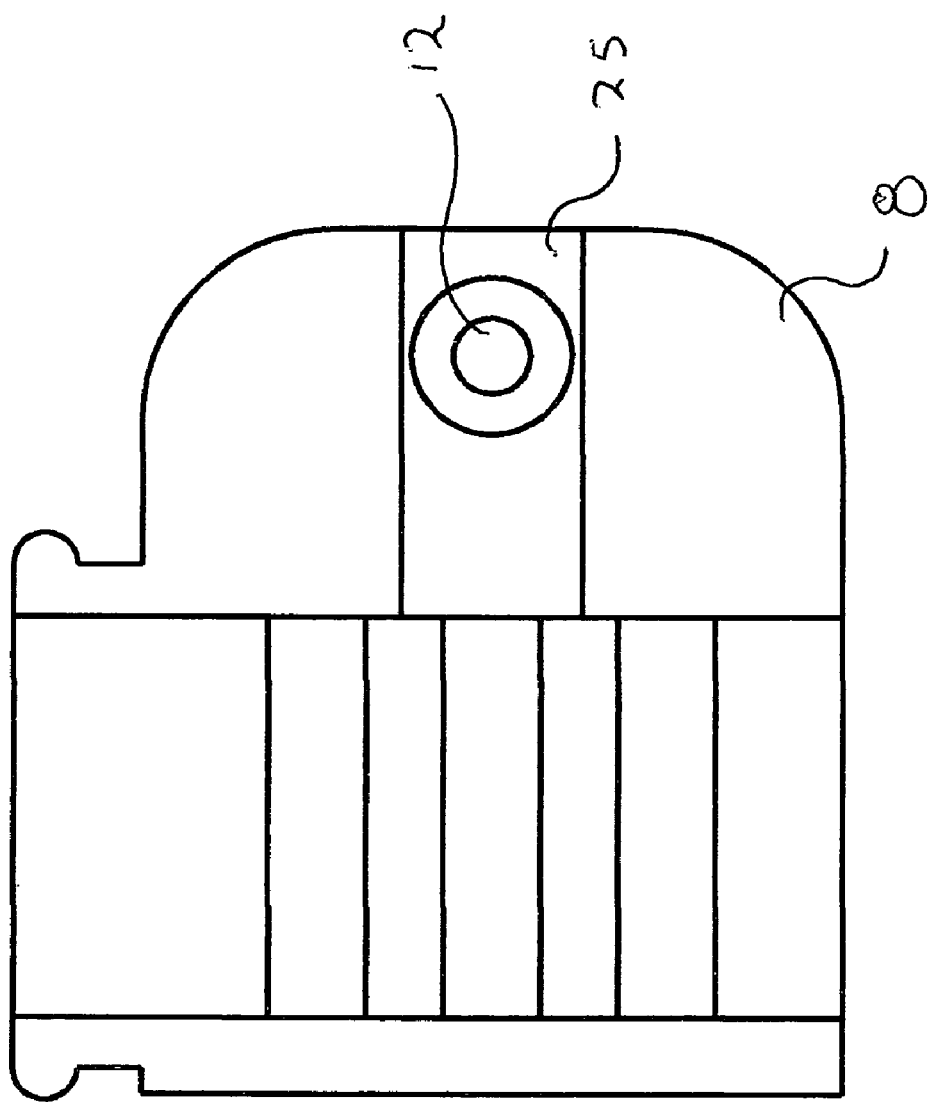

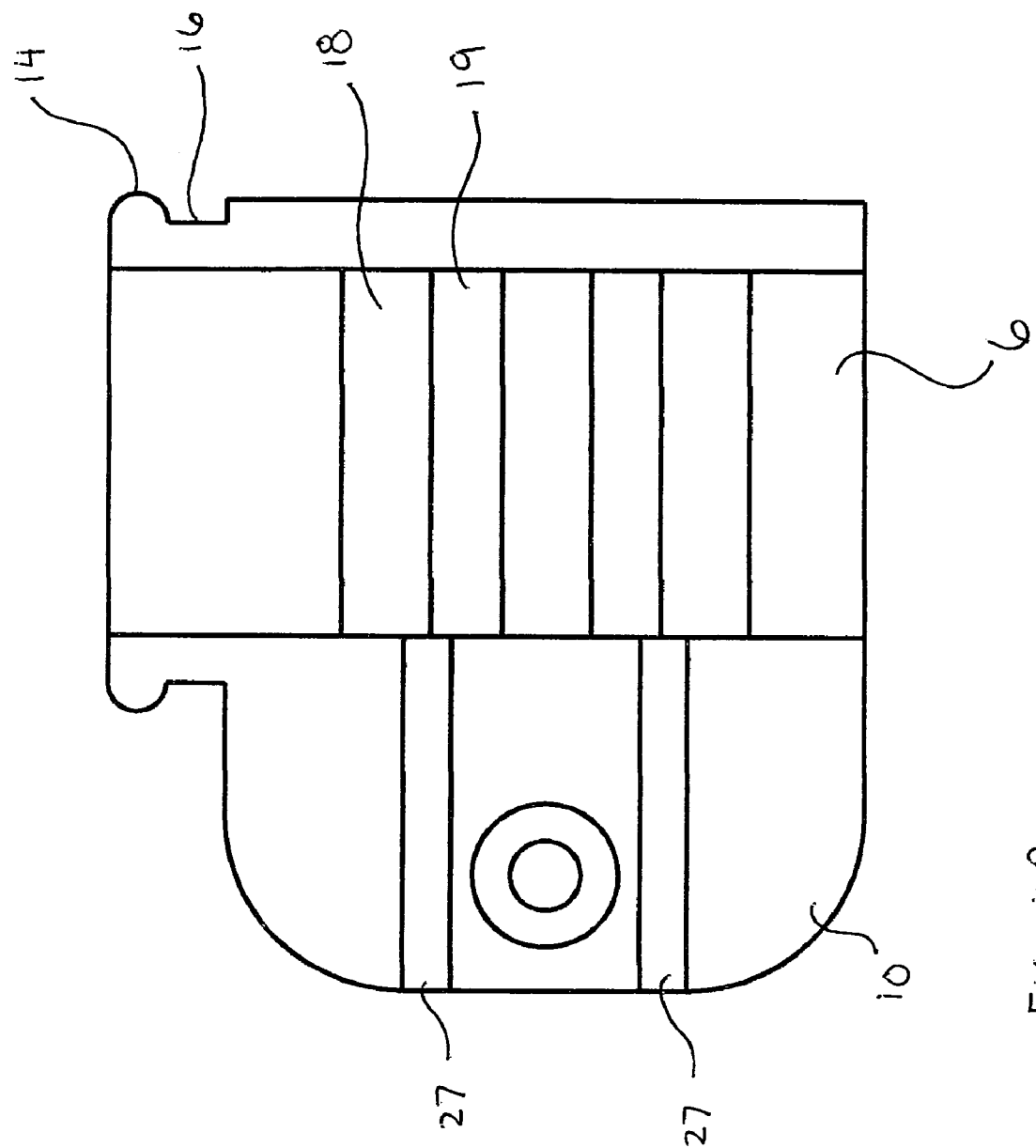

MEDICAL CLAMP AND METHOD OF USE

The present invention relates to a tapered tubular clamp, more specifically to an adjustable pressure split clamp that is designed to hold condom catheters on a penis or a medical sensor such as a pulse oximeter on a finger.

There is a plethora of clamps used in the medical industry for different purposes. One of the most common utilized is the close pin or alligator clamp style of device that is used to maintain a medical sensor in constant contact with the finger. These clamps have several design problems and as such are limited in what they can do. First they are not adjustable in their clamping pressure and size so as to properly fit extremely large or small fingers. Second they have two lines of contact on the finger rather than using the entire circumference of the finger for better gripping power. Third, they are designed to go over the tip of the finger and hold the sensor at that position. The end of the fingers are not the best location to monitor vital statistics as poor circulation, Reynaulds Syndrome or fake nails can severely impede or block the signal.

The present clamp offers an open ended, tapered split clamp design with a large thumbwheel operated pressure adjustment. This offers the ability to move the clamp up or down the finger to get a satisfactory reading. The size of the thumbwheel is large enough to allow people with disabilities to adjust it themselves, and the circular design allows for a much more secure clamping action while exerting less pressure on the finger than the conventional clamps.

The clamp is also suited for the retention of a condom catheter on the penis. Repeated insertion of catheters in males can cause irreparable damage including scarring, and commonly brings infectious bacteria into the body. In contrast condom catheters, being external by nature does not cause any of these problems, but are prone to slipping off and spilling, particularly as they fill with urine. This aspect of the condom catheter dissuades many practitioners from using these despite is medical advantages. This clamp has radiused edges internally and externally, an internal taper similar to that of a human penis (or finger) and is made in different sizes. Its tubular configuration and adjustable pressure allows gentle but firm gripping. Its configuration has an upper lip over which the elastic ring on the top of a condom catheter can be elastically deformed then retract in diameter to reside in a groove, thus reducing the possibility of accidental release of the catheter from the penis. Additionally, the clamp has a textured inside surface to increase the skin gripability and is ribbed on the outside to allow for air circulation to reduce sweating and to aid in the patient in positioning it. A set of opening wings allow for quick and easy release.

Henceforth, an improved medical clamp offering improved reliability, adjustment, gripability and condom catheter retention over conventional medical clamps would fulfill a long felt need in the medical industry. This new invention utilizes and combines known and new technologies in a unique and novel configuration to overcome the aforementioned problems and accomplish this.

SUMMARY OF THE INVENTION

The general purpose of the present invention, which will be described subsequently in greater detail, is to provide a new and improved medical clam that offers numerous distinct advantages in grippability, adjustment, placement and condom catheter retention. It has many of the advantages mentioned heretofore and many novel features that result in a new medical clamp which is not anticipated, rendered obvious, suggested, or even implied by any of the prior art, either alone or in any combination thereof.

In accordance with the invention, an object of the present invention is to provide an improved medical clamp capable of increased grippability to a human finger or penis.

It is another object of this invention to provide an improved medical clamp capable of adjustable pressure via a large thumbwheel that disabled or physically impaired patients can use.

It is a further object of this invention to provide a medical clamp capable of reliably retaining a condom catheter on the patient regardless of the volume of fluid building up inside.

It is still a further object of this invention to provide for a medical clamp that reduces sweating under the clamp, exerts a minimum of pressure yet generates a maximum of holding force.

It is yet a further object of this invention to provide an improved medical clamp ergonomically designed to fit the human body and capable of instant simple release.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements. Other objects, features and aspects of the present invention are discussed in greater detail below.

BRIEF DESCRIPTION OF THE DRAWINGS

FIG. 3 is a bottom view of the improved medical clamp without the thumbscrew but partially opened;

FIG. 4A is an inside view of the first body half of the improved medical clamp;

FIG. 4B is an inside view of the second body half of the improved medical clamp.

DETAILED DESCRIPTION

The present invention sets forth to resolve two problems in the medical industry, that of comfortably and securely retaining condom catheters on a patient without exerting enough force to pinch shut the urethra, and that of providing a finger clamp that adjusts to fit the patient as well as allowing different positioning of the clamp's sensors along the finger.

Figure 1:
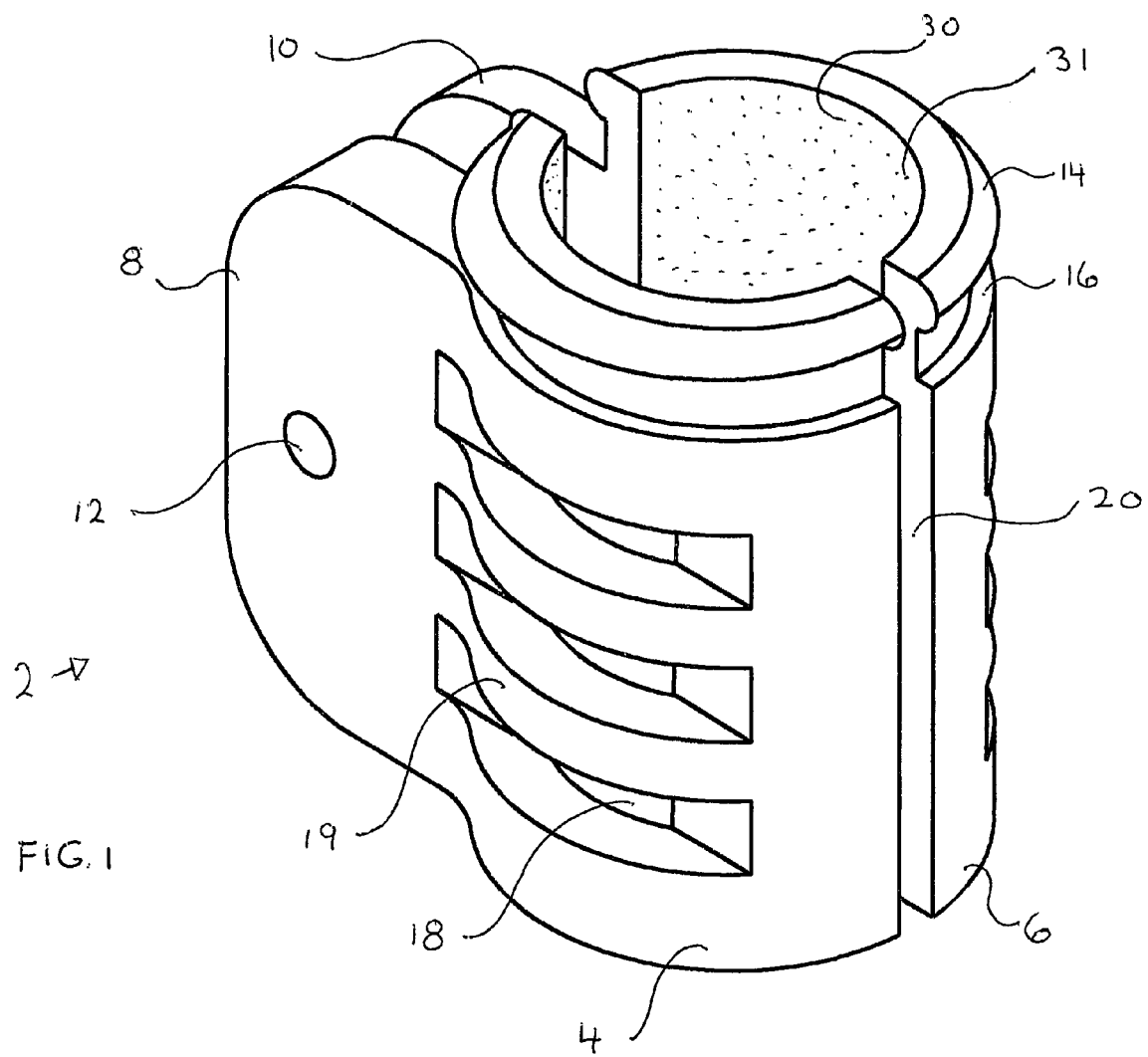
FIG. 1 is a perspective view of the improved medical clamp with the thumbscrew obscured from view.
Figure 5:
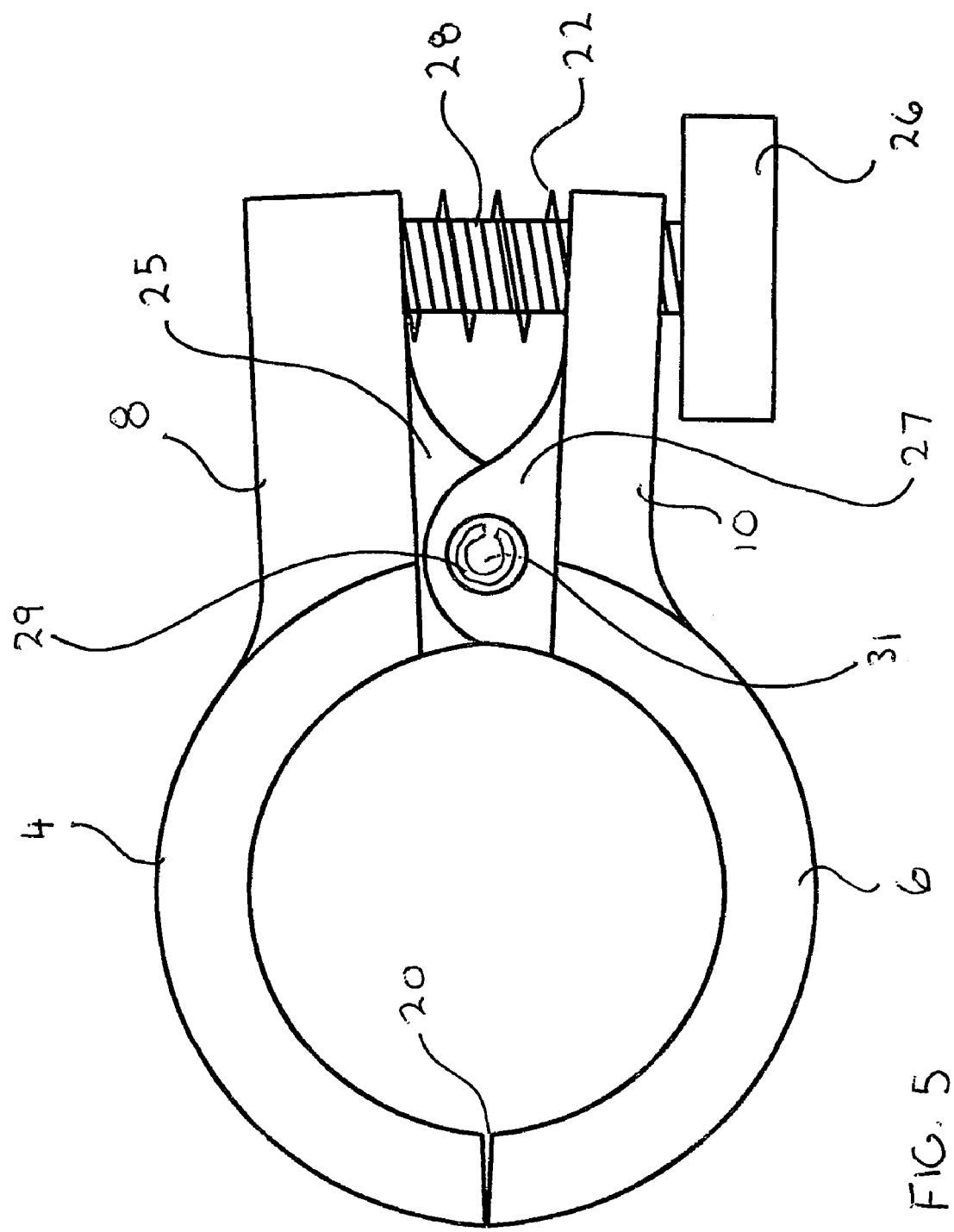
FIG. 5 is an end cross sectional view of the improved medical clamp showing the general arrangement of all parts.

Looking at FIG. 1 and FIG. 5 it can be seen that the improved medical clamp 2 has a first half 4 and a second half 6 each having a concave inner configuration (a semicircular axial cross section profile) so as to form an open ended tube when in the closed position. There is a first clamp wing 8 formed on and extending normally along the longitudinal axis of the body of the first half 4 and a second clamp wing 10 formed on and extending normally along the longitudinal axis of the body of the second half 10. the first clamp wing 8 has a threaded bore 12 formed there through and the second clamp wing 10 has a smooth orifice formed there through. The axes of these align to allow mating engagement of the threaded bore 12 with a thumbscrew formed from a threaded rod 28 that extends normally from the center of a thumbwheel 26. The first and second halves are not quite mirror image configurations and differ in the positioning of their interleaved hinge arms formed on the back of each clamp wing as illustrated in FIGS. 4A and 4B. The first clamp wing 8 has a single first hinge arm 25 formed on the inner surface thereof and the second clamp wing 10 has two second hinge arms 27 formed on its inner surface. Each of the interleaved hinge arms 25 have an aligned orifice 31 therein that allows a hinge pin 29 to pass through and frictionally engage each half. This hinge pin 29 allows the two halves of the clamp 2 to pivot about the pin 29 when the first clamp arm 8 and the second clamp arm 10 are forced toward each other. This opens a longitudinal slot 20 along the bottom of the clamp 2. (As illustrated in FIG. 4) Wire compression (coil) spring 22 is positioned between the clamp wings so as to exert pressure against the clamp wings forcing them apart and keeping the clamp 2 closed. The threaded rod 28 section of the thumbwheel 26 passes through the longitudinal center of the spring 22. If the thumbwheel 26 is rotated clockwise to threadingly engage the threaded bore 12 in the clamp wing deeper, then the clamp 2 will only close to a position that is partially opened such as shown in FIG. 3. This changes the overall diameter of the clamp dramatically but minimally changes the closing pressure exerted by the spring 22.

Figure 2:
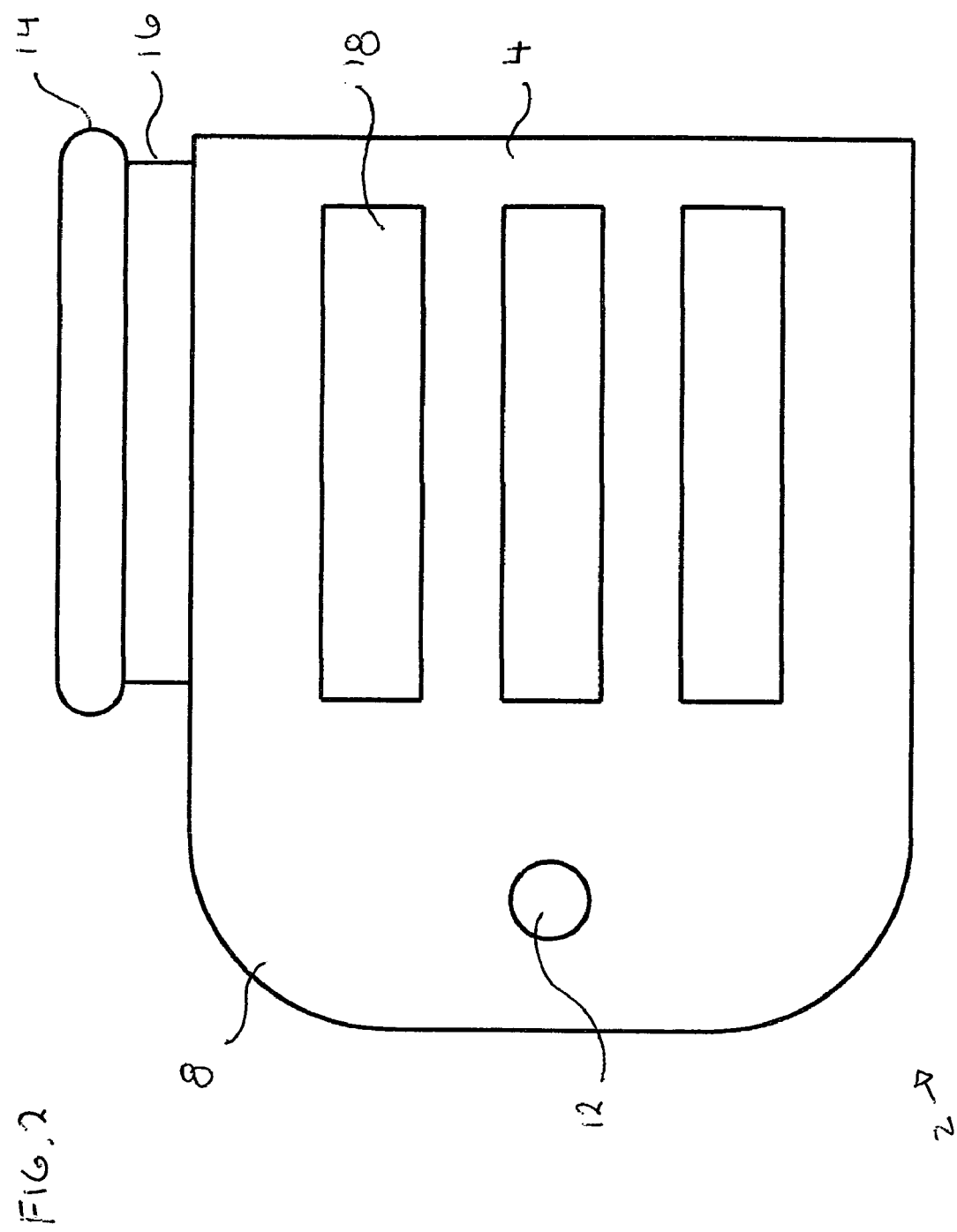
FIG. 2 is a side view of the first body half of the improved medical clamp with the thumbscrew removed.

Looking at FIG. 2 one can see the top circumferential condom catheter flange 14 and the condom catheter ring retention groove 16 formed about the outer top periphery of each of the halves. (It is to be noted that although FIG. 2 is a side view of the first body half of the improved medical clamp the side view of the second body half would appear as the mirror image since the clamp wing thickness, the orifices and the first and second hinge arms cannot be seen in side view.) This forces a condom catheter ring to be elastically deformed over the flange 14 to be enabled onto the clamp 2 and then allows it to constrict to its original size in the groove 16. Thus as the catheter fills with fluid and becomes heavier, it cannot slip off of the patient as he shifts in his wheelchair, unless a downward force is applied to the catheter to cause its ring to elastically deform enough to once again to go over the flange 14. Experimental tests have established a height profile for this flange 14 wherein a fully fluid filled condom catheter cannot develop enough gravitational force to exceed.

The internal concave configuration of the two haves, when assembled into a closed clamp configuration, has a tapered internal bore 30. Although this taper preferably decreases approximately 2 degrees across the longitudinal length of the body, (which has experimentally been shown to approximate the taper of a human finger and penis,) it is known that a taper of 1-5 degrees is acceptable for adequate gripping. It is also to be noted that the internal surface of each of the halves has a slight reticulated or matte finish 31 thereon to enhance grippability. Since the clamp 2 will cover a substantial length of the finger of penis, moisture buildup is an issue. For this reason each half has a set of vented ribs 19 with adjacent alternating through slots 18. This allows the human flesh to breath and prevents the unnecessary buildup of bacteria. The ribs 19 also form a grippable surface for an incapacitated patient to easily grip.

Basically the clamp wings 8 and 10 are compressed together so as to partially separate the clamp halves 4 and 6 making the clamp diameter increase. This allows the insertion of the finger clamp embodiment of the penis clamp embodiment to the placed over the body part and the clamp wings released to secure the clamp 2 to the body. The thumbscrew is then turned to open or close the clamp 2 (expand the internal diameter) to suit the patient. The thumbwheel 26 will bear against the second clamp wing 8 when the threaded rod 28 is threadingly engaged into threaded orifice 12 deep enough. This will restrict the size of the closed diameter of the clamp 2 yet allow the clamp wings to be squeezed together to open the clamp without further manipulation of the thumbscrew since the orifice on the second clamp wing 10 is not threaded.

All components of the medical clamp are made of a medical grade material, that is to say they are designed for repeated sterilization, washing and minimization of bacterial transport. For example the hinge pin 25 and the spring 22 are made of stainless steel and the body of the clamp is made from a non porous polymer that is FDA and medically approved.

The above description will enable any person skilled in the art to make and use this invention. It also sets forth the best modes for carrying out this invention. There are numerous variations and modifications thereof that will also remain readily apparent to others skilled in the art, now that the general principles of the present invention have been disclosed. The embedding of a sensor into an embodiment of the improved medical clamp utilized for measuring vital statistics from the patient's finger is well known in the art and requires mere mechanical aptitude.

Having thus described the invention, what is claimed as new and desired to be secured by Letters Patent is as follows:

1. A medical clamp comprising:
    a first half clamp body having an internal semicircular, axial cross section and a first planar flange extending therefrom said body that resides along a longitudinal axis thereof, and a first set of hinge arms formed thereon said flange with a hinge pin orifice formed therethrough;
    a second half clamp body having an internal semicircular, axial cross section and a second planar flange extending therefrom said body that resides along a longitudinal axis thereof and a second set of hinge arms formed thereon said second planar flange with a hinge pin orifice formed therethrough;
    a compression spring;
    a pivot pin; and
    a thumbscrew for adjusting the minimum closed internal diameter of the clamp without interfering with the opening of the clamp;
    wherein said first set of hinge arms are interleaved with said second set of hinge arms, and said pivot pin passes through said first set of hinge arm's a hinge pin orifices and through said second set of hinge arm's hinge pin orifices, wherein said first and said second half clamp bodies each have a longitudinal axis and a diameter of said axial cross section that decreases along the longitudinal axis of said bodies so as to form an internal tapered bore, wherein said pivot pin lies between said spring and said clamp's internal bore,
    and wherein said compression spring is positioned about said thumbscrew, between said first planar flange and said second planar flange so as to exert pressure on said flanges and cause said first half clamp body and said second half clamp body to pivot about said hinge pin, and wherein said first planar flan e has a threaded bore formed therethrough, said second planar flange has an orifice formed therethrough and said threaded thumbscrew passes through said orifice and matingly engages said threaded bore.

2. The medical clamp of claim 1 wherein said first and said second half bodies have a semicircular internal surface with a matte finish on said surface.

3. The medical clamp of claim 2 wherein said first and said second half bodies have alternating ribs and through passages formed thereon.

4. The medical clamp of claim 1 wherein said first and said second half bodies have alternating ribs and through passages formed thereon.

5. The medical clamp of claim 1 wherein said taper is less than 6 degrees.

6. The medical clamp of claim 1 wherein said taper is less than 2 degrees.

* * * * *